(12) United States Patent
Pasqualini

(10) Patent No.: US 8,070,952 B2
(45) Date of Patent: Dec. 6, 2011

(54) APPARATUS AND METHOD FOR THE TREATMENT OF BLOOD

(75) Inventor: Gianni Pasqualini, Rovigo (IT)

(73) Assignee: Medical Service S.R.L. (IT)

( * ) Notice: Subject to any disclaimer, the term of this patent is extended or adjusted under 35 U.S.C. 154(b) by 546 days.

(21) Appl. No.: 12/112,451

(22) Filed: Apr. 30, 2008

(65) Prior Publication Data

US 2008/0243045 A1 Oct. 2, 2008

Related U.S. Application Data

(63) Continuation-in-part of application No. 10/823,412, filed on Apr. 13, 2004, now abandoned.

(30) Foreign Application Priority Data

Oct. 3, 2003 (IT) .............................. TO2003A0785

(51) Int. Cl.
*B01D 61/00* (2006.01)
*B01D 61/24* (2006.01)
*B01D 61/28* (2006.01)
*A61M 1/14* (2006.01)
*A61M 1/16* (2006.01)
*A61M 1/18* (2006.01)

(52) U.S. Cl. ..... 210/645; 210/188; 210/194; 210/195.1; 210/203; 210/314; 210/321.6; 210/321.72; 210/321.79; 210/321.8; 210/321.89; 210/335; 210/433.1; 210/436; 210/472; 210/500.21; 210/644; 422/44; 422/45; 422/46; 422/48

(58) Field of Classification Search .................. 210/188, 210/194, 195.1, 203, 314, 321.6, 321.72, 210/321.79, 321.8, 321.88, 321.89, 335, 210/433.1, 436, 472, 500.21, 644, 645, 650, 210/651; 422/44, 45, 46, 48; 604/405
See application file for complete search history.

(56) References Cited

U.S. PATENT DOCUMENTS

| | | | |
|---|---|---|---|
| 3,768,977 A | 10/1973 | Brumfield et al. |
| 3,769,162 A | 10/1973 | Brumfield |
| 3,807,958 A | 4/1974 | Brumfield et al. |
| 5,266,265 A | 11/1993 | Raible |
| 2002/0077581 A1 | 6/2002 | Davidner et al. |
| 2002/0176798 A1 | 11/2002 | Linker et al. |
| 2004/0143207 A1 | 7/2004 | Torre |

FOREIGN PATENT DOCUMENTS

| | | |
|---|---|---|
| EP | 0705610 | 4/1996 |
| EP | 0890368 | 1/1999 |
| EP | 1180374 | 2/2002 |

*Primary Examiner* — John Kim
(74) *Attorney, Agent, or Firm* — The Webb Law Firm

(57) ABSTRACT

The invention relates to an apparatus and method for simultaneous extrarenal blood purification therapy and respiration support therapy. The apparatus includes a $CO_2$ removing means having a first inlet for receiving a flow of blood for $CO_2$ removal and a first outlet for expelling blood deprived of $CO_2$. The apparatus also includes filtering means having a first inlet for receiving the flow of blood, a first outlet for expelling purified blood, and at least one drain channel. The drain channel directs a diluting liquid obtained from the blood expelled during purification of the blood. The drain channel is directly connected to the first inlet of the $CO_2$ removing means to supply the diluting liquid to the $CO_2$ removing means without submitting the diluting liquid to any filtering treatment during passage along the drain channel.

16 Claims, 5 Drawing Sheets

APPARATUS AND METHOD FOR THE TREATMENT OF BLOOD

CROSS-REFERENCE TO RELATED APPLICATION

This application claims priority to U.S. application Ser. No. 10/823,412 filed Apr. 13, 2004, which claims the benefit of Italian Patent Application No. TO2003A 000785, filed Oct. 3, 2003, the entire contents of each of which are hereby incorporated by reference.

BACKGROUND OF THE INVENTION

1. Field of the Invention

The present invention relates generally to a method and apparatus for the treatment of blood and, more specifically, to a method and an apparatus which can be used for permitting respiration support therapy on a patient.

2. Description of Related Art

Extrarenal blood purification systems or so-called "haemofiltration systems" exist which provide for purifying the patient's blood of waste liquids and/or soluble substances which accumulate in the blood for pathological and/or surgical reasons, and/or as a result of substances administered to the patient. Such haemofiltration systems thus perform the functions normally carried out by healthy kidneys in correct working condition.

Haemofiltration systems of the above-type normally include a blood purification circuit, along which the patient's blood, is fed to add any necessary supplements and/or to purify it of any toxic solutes. The blood purification circuit is connected to the patient by two feed conduits or catheters: one for supplying the non-purified venous blood of the patient to the purification circuit, and the other for feeding the purified blood into the patient's vein.

The purification circuit normally includes a pump connected to a first catheter by a conduit for receiving the patient's blood, which pumps the patient's blood along the purification circuit. The purification circuit also includes a unit for adding an anticoagulant to the blood, and a heating and supplementing unit for adding a liquid supplement to the blood and heating the liquid supplement to a predetermined temperature. The purification circuit also includes a blood purifying filter, or so-called haemofilter, which is connected to the second catheter, and provides for eliminating any toxic elements in the blood before it is fed back to the patient's body.

In certain patients in particularly critical condition, extrarenal purification therapy must very often be accompanied by respiration support therapy, by which the oxygen concentration of the patient's blood is supplemented by removing excess carbon dioxide ($CO_2$) from the blood. Although the above-described systems provide for highly effective extrarenal blood purification, they fail to provide for simultaneous respiration support therapy. Accordingly, the above-described systems require that the patient must be ventilated by non-physiological means during extrarenal purification therapy, with obvious drawbacks and discomfort to the patient.

United States Patent Application No. 2004/0143207 describes a blood treatment apparatus which can be used in a continuous renal replacement therapy (CRRT) capable of carrying out the so called "decapneization" of blood, in other words, of removing $CO_2$ from the blood itself. This apparatus is provided with a blood deputation circuit through which the patient's blood passes, so that any substances to be reintegrated can be purified from any toxic solutes. It is connected to the patient by means of a first catheter which conveys the blood to be depurated, which flows inside the patient's vein into the blood deputation circuit, and a second catheter which conveys the depurated blood back into the patient's vein.

The deputation circuit consists of a pump which is disposed and acts downstream of the first catheter so that it receives the patient's blood and puts it into circulation inside the deputation circuit of a unit in order to add an anticoagulant to the blood. The circuit includes a heating and reintegration unit capable of adding a suitable reintegration liquid to the blood and to bring it to a predetermined temperature. The circuit also consists of a blood depuration filter (the "haemofilter") connected to the second catheter to eliminate the toxic elements present in the blood before it is introduced again into the patient's body. When inserted in the deputation system described above, the apparatus of United States Patent Application No. 2004/0143207 consists of a hoxygenator; in fact, for some patients whose health conditions are particularly serious, it is necessary to accompany the external renal depuration therapy with a respiratory support therapy and to remove the excessive amount of carbon dioxide from the blood itself. If the patient does not need a substitutive renal therapy, that is to say if the patient's renal functions are correct, the CRRT therapy is not necessary, and it even may be harmful.

SUMMARY OF THE INVENTION

In accordance with the present invention, it is possible to provide a support for the mechanical and/or assisted ventilation to which a patient is submitted by keeping said ventilation within the limits of the so called "protective ventilation", that is to say within values which are decreased by the volume and by the plateau pressure.

An advantage of the present invention is that blood submitted to a carbon dioxide removal treatment is diluted using the patient's plasmatic water with the consequent elimination of the devices used for adding reintegration liquids. Another advantage of the present invention is that veno-venous access to the patient is foreseen by transcutaneous way, without surgical exposition of the vessels to which the equipment is to be connected. Another advantage of the present invention is that the therapy can be carried out for days, even for weeks, so patients can easily tolerate it. In one embodiment, flows are preferably kept below 400 mil/min. Another advantage of the present invention is the easy control guaranteed by the transcutaneous access and the relatively low flow allows for the use of the apparatus and the corresponding therapy method in resuscitation. The invention is also used as a support to mechanical ventilation as said ventilation is kept within the safety parameters. The equipment consists of an extremely limited number of components, so it is easy to use and to build, moreover its features remain basically unchanged during use. Finally, the apparatus features relatively few connections for the circuit into which the blood passes so as to consequently determine a reduction of the circuit filling volume (priming).

In one embodiment of the present invention, a blood treatment method for the simultaneous extrarenal blood purification therapy and respiration support therapy includes the step of providing a blood purification circuit connected to a patient's cardiocirculatory system by two blood feed conduits. The circuit includes a first conduit for receiving blood from the patient's cardiocirculatory and supplying blood to the blood purification circuit. The circuit also includes a second conduit in communication with a patient's vein to feed purified blood back into the patient's cardiocirculatory system. The circuit also includes filtering means having a first inlet for receiving blood for purification in communication, and a first outlet for expelling purified blood. The circuit also includes $CO_2$ removing means having a first inlet for receiving a flow of blood for $CO_2$ removal and a first outlet for expelling blood deprived of $CO_2$. The circuit also includes a drain channel for directing a diluting liquid separated from the purified blood by the filtering means to the $CO_2$ removing means, wherein the drain channel is directly connected to the first inlet of the $CO_2$ removing means. The method also includes the steps of directing blood through the filtering means, directing blood through the $CO_2$ removing means, and supplying the diluting liquid to the $CO_2$ removing means through the drain channel which is directly connected to the first inlet of the $CO_2$ removing means.

The first outlet of the $CO_2$ removing means may be connected to the first inlet of the filtering means to supply to the filtering means blood deprived of $CO_2$. The circuit may also include a pump for supplying the diluting liquid to the $CO_2$ removing means at a flow rate of about 53 ml/min. The circuit may further include a pump for pumping the blood within the blood purification circuit at a flow rate of about 350 ml/min.

In another embodiment of the present invention, a blood treatment unit for simultaneous extrarenal blood purification therapy and respiration support therapy includes $CO_2$ removing means having a first inlet for receiving a flow of blood for $CO_2$ removal, and a first outlet for expelling blood deprived of $CO_2$. The filtering means includes a first inlet for receiving the flow of blood, a first outlet for expelling purified blood, and at least one drain channel by which, in use, a diluting liquid obtained from the blood is expelled during purification of the blood. The drain channel is directly connected to the first inlet of the $CO_2$ removing means to supply the diluting liquid to the $CO_2$ removing means, without submitting the diluting liquid to any filtering treatment during passage along the drain channel.

In one configuration, the blood treatment unit includes pumping means connecting the drain channel of the filtering means to the first inlet of the $CO_2$ removing means to pump the diluting liquid, obtained from the blood by the filtering means, to the $CO_2$ removing means. The filtering means may be at least partially integrated with the $CO_2$ removing means. In another configuration, the $CO_2$ removing means includes an inner seat which houses the filtering means. Optionally, the $CO_2$ removing means includes a first casing having at least one membrane for removing $CO_2$ from the blood. Alternatively, the $CO_2$ removing means may include a first casing having a plurality of membranes for removing $CO_2$ from the blood.

In another embodiment of the present invention, a blood treatment unit for simultaneous extrarenal blood purification therapy and respiration support therapy includes $CO_2$ removing means having a first inlet for receiving a flow of blood for $CO_2$ removal, and a first outlet for expelling blood deprived of $CO_2$. The blood treatment unit also includes filtering means having a first inlet for receiving a flow of blood for purification, and a first outlet for expelling purified blood. The first outlet of the $CO_2$ removing means may be connected to the first inlet of the filtering means to supply to the filtering means blood deprived of $CO_2$. The filtering means may also include at least one drain channel by which, in use, a diluting liquid obtained from the blood is expelled during purification of the blood. The drain channel is directed connected to the first inlet of the $CO_2$ removing means to supply the diluting liquid to the $CO_2$ removing means. The $CO_2$ removing means includes an inner seat housing the filtering means, and a first casing having at least one membrane for removing $CO_2$ from the blood. The filtering means includes a second casing housed inside the first casing having at least one blood purifying membrane.

In one configuration, the first casing includes a plurality of membranes for removing $CO_2$ from the blood. Optionally, the membranes for removing $CO_2$ from the blood are interposed between the first casing and the second casing. The $CO_2$ removing means may include a container internally defining the inner seat, and interposed between the membranes for removing $CO_2$ from the blood and the second casing. In another configuration, the second casing includes a plurality of blood purifying membranes.

In yet another embodiment of the present invention, a blood treatment apparatus includes a blood depuration circuit connected to a patient's cardiocirculatory system, and a pump for moving blood within the blood depuration circuit. The apparatus also includes a hoxygenator for removing $CO_2$ from the blood, with the hoxygenator disposed downstream of the pump. The apparatus further includes a haemofilter which separates plasmatic water from the blood, with the haemofilter disposed downstream of the hoxygenator. The haemofilter includes an output for expelling plasmatic water connected to the depuration circuit upstream of the hoxygenator.

Optionally, the output of the haemofilter is connected to the depuration circuit by a duct. In one configuration, the apparatus includes a pump for moving the plasmatic water within the duct. Further, the depuration circuit may include a plurality of sensors connected to corresponding control means for monitoring blood and/or plasmatic water within the depuration circuit.

BRIEF DESCRIPTION OF THE DRAWINGS

A non-limiting embodiment of the present invention will be described by way of example with reference to the accompanying drawings, in which.

DESCRIPTION OF A PREFERRED EMBODIMENT

Figure 1:
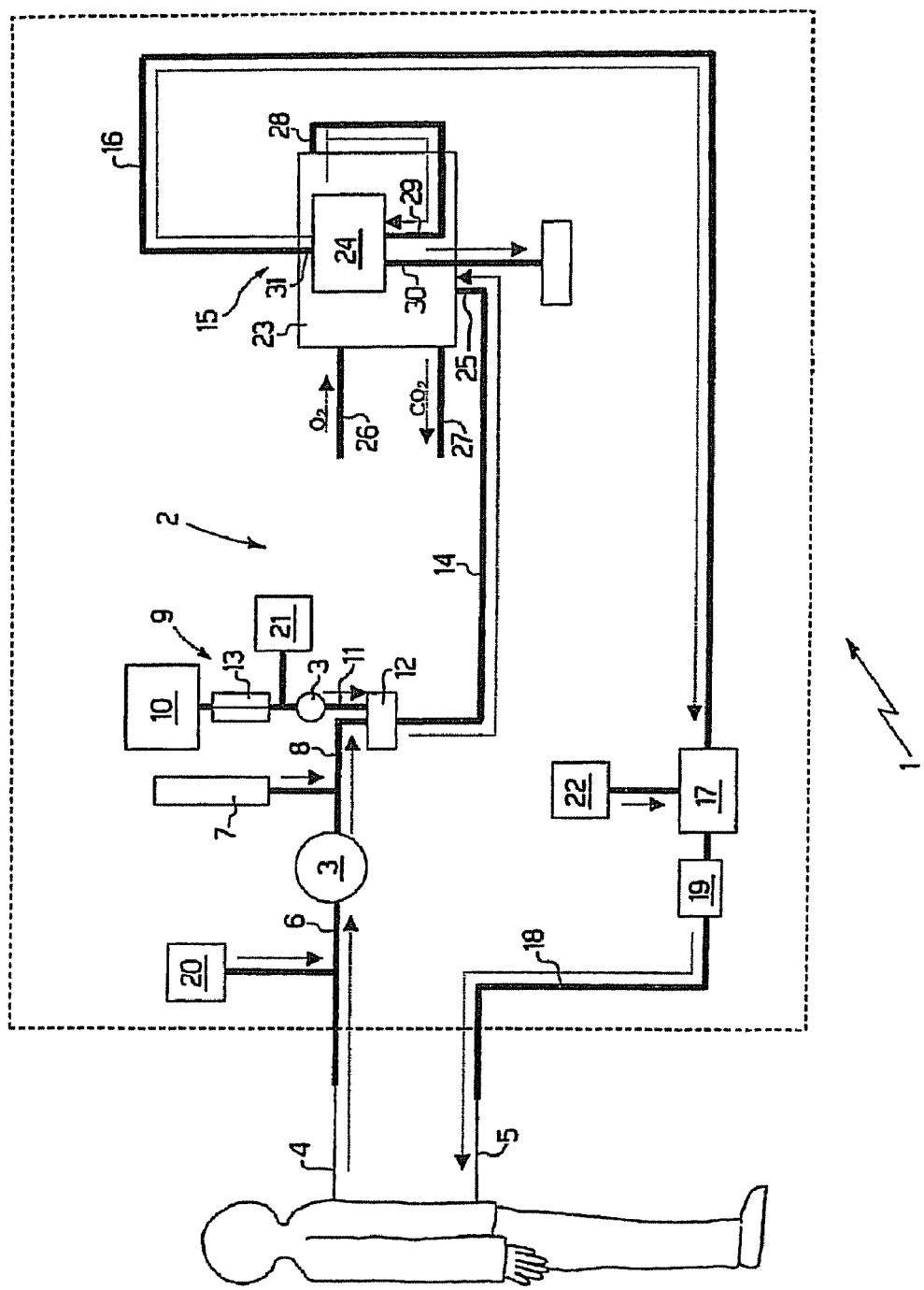
FIG. 1 is a schematic representation of a blood treatment apparatus in accordance with an embodiment of the present invention.

FIG. 1 shows a machine designed to permit simultaneous extrarenal blood purification therapy, i.e. haemofiltration, and respiration support therapy of a patient. Machine 1 substantially comprises a blood purification circuit 2, along which the patient's blood is fed to add liquid supplements and to purify it of any waste solutes and/or toxic elements; and one or more flow pumps 3 to maintain a given blood flow along blood purification circuit 2.

Blood purification circuit 2 is connected to the patient's cardiocirculatory system by two blood feed conduits or catheters, one of which, indicated hereinafter by 4, receives and supplies blood from the patient's vein to blood purification circuit 2, while the other, indicated hereinafter by 5, is inserted inside a vein to feed the purified blood back into the patient's cardiocirculatory system.

In the example shown, blood purification circuit 2 comprises an inlet conduit 6 connecting catheter 4 to flow pump 3; and a unit 7 for adding an anticoagulant to the blood, and which is connected to an outlet conduit 8 of flow pump 3 to add the anticoagulant to the blood flow. In the example shown, unit 7 may be defined by a tank 10 containing anticoagulant such as heparin or similar.

With reference to FIG. 1, blood purifying circuit 2 also comprises a supplementing unit 9 for appropriately heating a liquid supplement or infusion to a given temperature and then adding it to the blood flowing in purification circuit 2. In the example shown, supplementing unit 9 comprises a tank 10 containing the liquid supplement or infusion; a conduit 11 connecting tank 10 to a connecting member 12 via a flow pump 3; and a heating device 13 connected to conduit 11 between flow pump 3 and tank 10 to heat the liquid supplement or infusion before it is mixed with the blood. In addition to conduit 11, connecting member 12 is also connected at the inlet to the outlet conduit 8 of tank 7, and provides for "mixing" the heated liquid supplement or infusion with the blood, and feeding the blood to an outlet conduit 14.

Purification circuit 2 also comprises a blood treatment unit 15 for both removing excess $CO_2$ from the blood, thus performing respiration support therapy, and ultrafiltering the blood of waste substances and/or liquids, thus performing extrarenal purification therapy.

In the example shown, blood treatment unit 15 is connected at the inlet to the outlet conduit 14 of connecting member 12 to receive the mixed blood for $CO_2$ removal and purification, and is connected at the outlet, by a conduit 16, to a blood collecting vessel 17, in turn connected at the outlet to catheter 5 by a connecting conduit 18. In the example shown, blood collecting vessel 17 may be defined, for example, by a known venous blood collecting tank not described in detail.

An air detecting device 19 is fitted along connecting conduit 18, i.e. downstream from blood collecting vessel 17, to remove from the blood any air bubbles which, if transmitted to the patient, could produce an embolism or other serious consequences.

Preferably, though not necessarily, purification circuit 2 also comprises a pressure gauge 20 connected to inlet conduit 6, upstream from flow pump 3, to measure the "intake" pressure of the blood from the patient; a pressure gauge 21 connected to conduit 11 to measure the pressure of the liquid supplement from tank 10; and a pressure gauge 22 cooperating with blood collecting vessel 17 to measure the pressure of the blood to be fed back into the patient's cardiocirculatory system.

Figure 2:
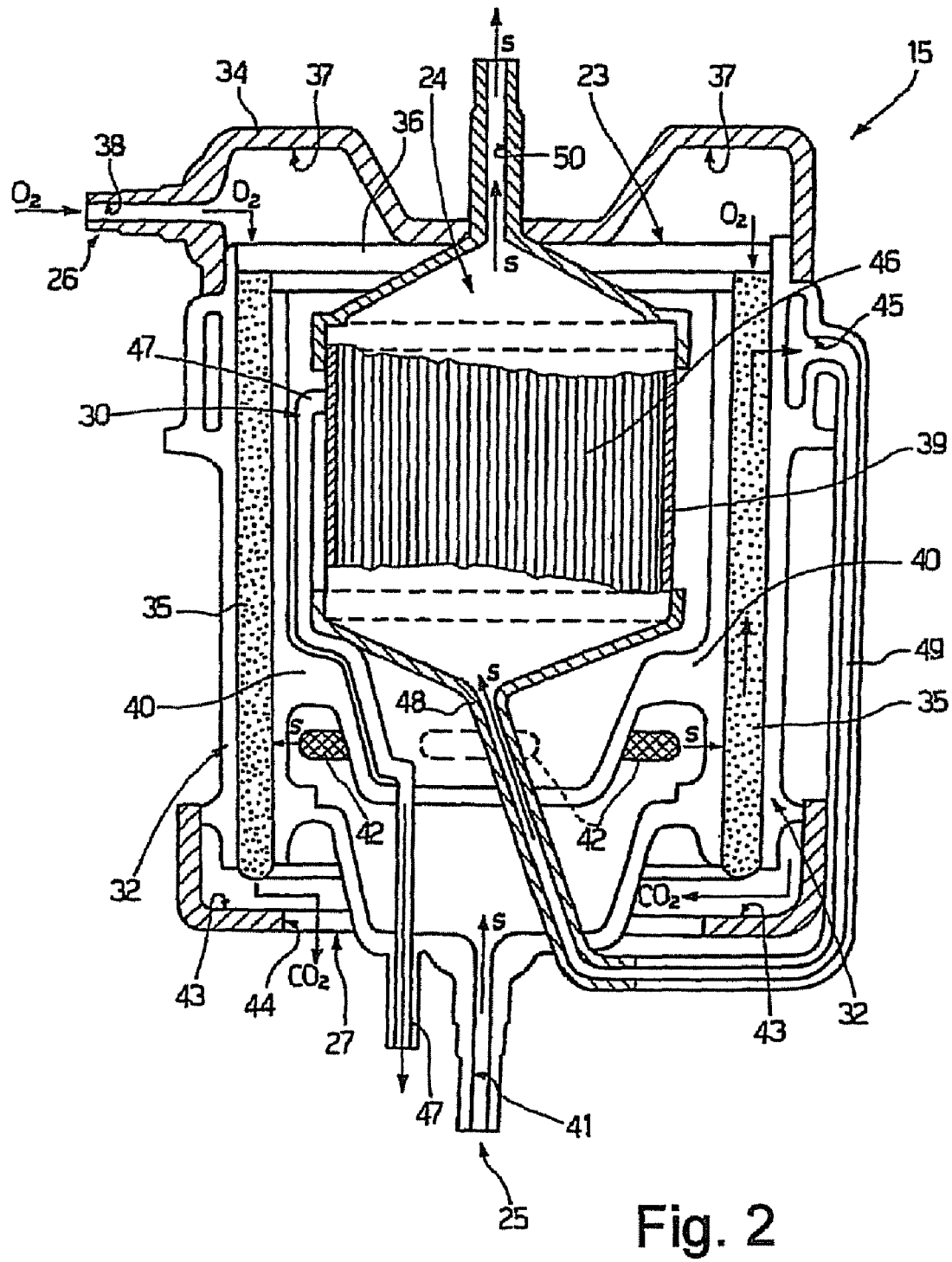
FIG. 2 is a cross-sectional view of the blood treatment unit of FIG. 1.

Treatment unit 15 comprises a $CO_2$ removing device 23 and a filter 24, which, as shown schematically in FIGS. 1 and 2, are integrated to form one body, and provide respectively for eliminating a given amount of $CO_2$ from the blood, and ultrafiltering the blood of waste liquids and substances and/or toxic substances.

In the example shown schematically in FIG. 1, $CO_2$ removing device 23 is connected to filter 24 so that filter 24 is substantially integrated in $CO_2$ removing device 23. More specifically, $CO_2$ removing device 23 houses filter 24 and is connected upstream from filter 24 with respect to the blood flow direction along purifying circuit 2.

As shown in FIG. 1, $CO_2$ removing device 23 device 23 has an inlet 25 connected to conduit 14 to receive the blood for $CO_2$ removal and purification, an inlet 26 connectable to an oxygen cylinder or tank (not shown) to receive a predetermined amount of oxygen by which to remove $CO_2$ from the blood, an exhaust outlet 27 from which $CO_2$ removed from the blood is expelled, and an outlet 28 for the blood deprived of $CO_2$.

Filter 24 is connected downstream from $CO_2$ removing device 23, and has an inlet 29 connected to and supplied with blood deprived of $CO_2$ by outlet 28 of $CO_2$ removing device 23, an outlet 30 for expelling the ultrafiltrate containing the waste liquids and toxic and/or waste substances filtered from the blood, and an outlet 31 supplying to conduit 16 the blood purified and deprived of $CO_2$.

With reference to FIG. 2, as stated, $CO_2$ removing device 23 and filter 24 defining treatment unit 15 are advantageously integrated to form one body.

More specifically, treatment unit 15 comprises two airtight containers or casings made of rigid material, such as polycarbonate or similar and arranged one inside the other to define a seat 32 in between.

The outer casing 34 is tubular, preferably, though not necessary, in the form of a cylinder or parallel pipes, and houses, in the gap defined by seat 32, a bundle of membranes 35, through and/or over which oxygen and a stream of pressurized blood flow in use, so that the haemoglobin in the blood releases $CO_2$ and simultaneously acquires oxygen to remove $CO_2$ from the blood.

Membranes 35 may be defined by a number of sheets or hollow fibres of polypropylene or similar material, and are arranged parallel to preferably occupy a central portion of seat 32.

The hollow fibres may obviously be arranged in any manner inside seat 32, e.g., crossed and/or wound to form a predetermined oxygen-blood exchange surface of, say, roughly 0.6-0.7 $m^2$. In the FIG. 2 example, the top of the bundle of membranes 35 is connected rigidly to the top end of outer casing 34 by a supporting plate 36, which extends outwards to define, with the inner wall of the top end, a top gap 37 communicating with the outside of outer casing 34 via an oxygen inlet channel 38 defining inlet 26 of $CO_2$ removing device 23.

More specifically, as shown clearly in FIG. 2, oxygen inlet channel 38 is formed in the lateral wall of outer casing 34, and feeds the oxygen through gap 37 downwards (arrow $O_2$), i.e., towards membranes 35.

In the gap between membranes 35 and the inner casing, hereinafter indicated 39, a bell-shaped member 40 is fitted beneath plate 36, is closed at the top by plate 36, and has, at the opposite end, an inlet channel 41 defining inlet 25 of $CO_2$ removing device 23. In the example shown, inlet channel 41 extends through the centre of the bottom end of outer casing 34, and provides for feeding the blood for $CO_2$ removal and purification (arrow S) into bell-shaped member 40.

At the bottom end of the bundle of membranes 35, bell-shaped member 40 has a number of through holes 42, through which, in use, the pressurized blood inside bell-shaped member 40 is pushed out towards membranes 35.

The bottom end of outer casing 34 and the bottom portion of bell-shaped member 40 define a bottom gap 43 communicating with membranes 35 and for receiving the $CO_2$ released by the haemoglobin in the blood during oxygenation. As shown clearly in the FIG. 2 example, bottom gap 43 communicates externally (arrow $CO_2$) via a $CO_2$ exhaust channel 44 formed in the bottom end of outer casing 34 and defining outlet 27 of $CO_2$ removing device 23.

With reference to FIG. 2, at the top of membranes 35, beneath plate 36, the lateral wall of outer casing 34 has an outlet channel 45 for the blood from $CO_2$ removing device 23, and from which $CO_2$ has been removed.

Inner casing 39 is tubular, preferably, though not necessarily, in the form of a cylinder or parallel pipes, and is fixed rigidly by one end to a corresponding end of outer casing 34. More specifically, in the FIG. 2 example, inner casing 39 is housed inside bell-shaped member 40, and is connected rigidly at the top end to the top end of outer casing 34.

Inner casing 39 in turn houses a number of highly permeable, semi-permeable membranes 46 which, when subjected to hydrostatic pressure, provide for ultrafiltrating the blood to eliminate toxic elements dissolved in the blood.

More specifically, in the FIG. 2 example, semi-permeable membranes 46 are preferably, though not necessarily, defined by a bundle of hollow fibres made of highly permeable polysulphone, arranged substantially parallel, and along which the blood for filtering flows in use.

As ultrafiltration removes a considerable amount of liquid from the blood, inner casing 39 has a drain channel 47 for expelling the liquids and toxic elements removed from the blood. More specifically, drain channel 47 defines outlet 30 of filter 24, and, as shown in the FIG. 2 example, extends from a lateral wall of and at the top end of inner casing 39, and partly through bell-shaped member 40 to come out inside outer casing 34.

Inner casing 39 also comprises a blood inlet channel 48, which is connected by a connecting conduit 49 to outlet channel 45 of outer casing 34, from which it receives the blood deprived of $CO_2$.

As shown clearly in the FIG. 2 example, blood inlet channel 48 is formed in the bottom end of inner casing 39, and connecting conduit 49 extends from blood inlet channel 48, along an inner portion of bell-shaped member 40, and preferably, though not necessarily, comes out outside outer casing 34 to connect up with outlet channel 45 of outer casing 34.

At the top end of inner casing 39, opposite blood inlet channel 48, a blood outlet channel 50 is provided for the blood purified and deprived of $CO_2$. In the FIG. 2 example, blood outlet channel 50 defines outlet 31 of filter 24, extends through the center of the top end of outer casing 34, and comes out outside outer casing 34.

When machine 1 is operated, flow pump 3 receives and feeds the blood from catheter 4 to connecting member 12, while at the same time unit 7, adds anticoagulant to the blood, and connecting member 12 mixes the blood with the liquid supplement supplied by supplementing unit 9, and feeds the blood to treatment unit 15.

At treatment unit 15, the blood flows along inlet channel 41, and is forced by pressure inside bell-shaped member 40 and out through holes 42 towards the bottom end of the bundle of membranes 35.

The pressurized blood forced upwards flows over and/or through membranes 35, while, at the opposite end, the oxygen flowing in from channel 38 and through top gap 37 is directed towards the top of membranes 35, flows through and/or over membranes 35, and gradually downwards in the opposite direction to the blood flow. As it flows through membranes 35, the haemoglobin in the blood acquires oxygen and releases excess $CO_2$, which flows to the bottom of outer casing 34, through bottom gap 43, and out through exhaust channel 44.

$CO_2$ removal from the ultrafiltrate is completed by the time the blood reaches the top of the bundle of membranes 35, where outlet channel 45 feeds the flow of the blood deprived of $CO_2$ along conduit 49 to inlet channel 48 of inner casing 39, inside which purification takes place.

The incoming blood from inlet channel 48 encounters and flows through semi-permeable membranes 46, which separate the blood from the waste substances and/or toxic substances and surplus liquids, which are expelled from inner casing 39 along drain channel 47; and the pressurized blood is forced gradually towards outlet channel 50, from which it flows out purified.

At this point, the blood flows through blood collecting vessel 17 and air detecting device 19, and back into the patient's cardiocirculatory system along catheter 5.

Machine 1 as described above is extremely advantageous, in that, integrating $CO_2$ removing device 23 and filter 24 in one body, i.e. one treatment unit 15, permits simultaneous respiration support and extrarenal purification therapy, thus eliminating the need for non-physiological ventilation of the patient, with obvious benefits to the patient.

It should be pointed out that, besides reducing the size of treatment unit 15, integration of $CO_2$ removing device 23 and filter 24 in one treatment unit 15 also simplifies connection of the various inlet/outlet conduits to purification circuit 2, so that treatment unit 15 can be assembled faster, with less likelihood of the circuit being connected wrongly.

Figure 3:
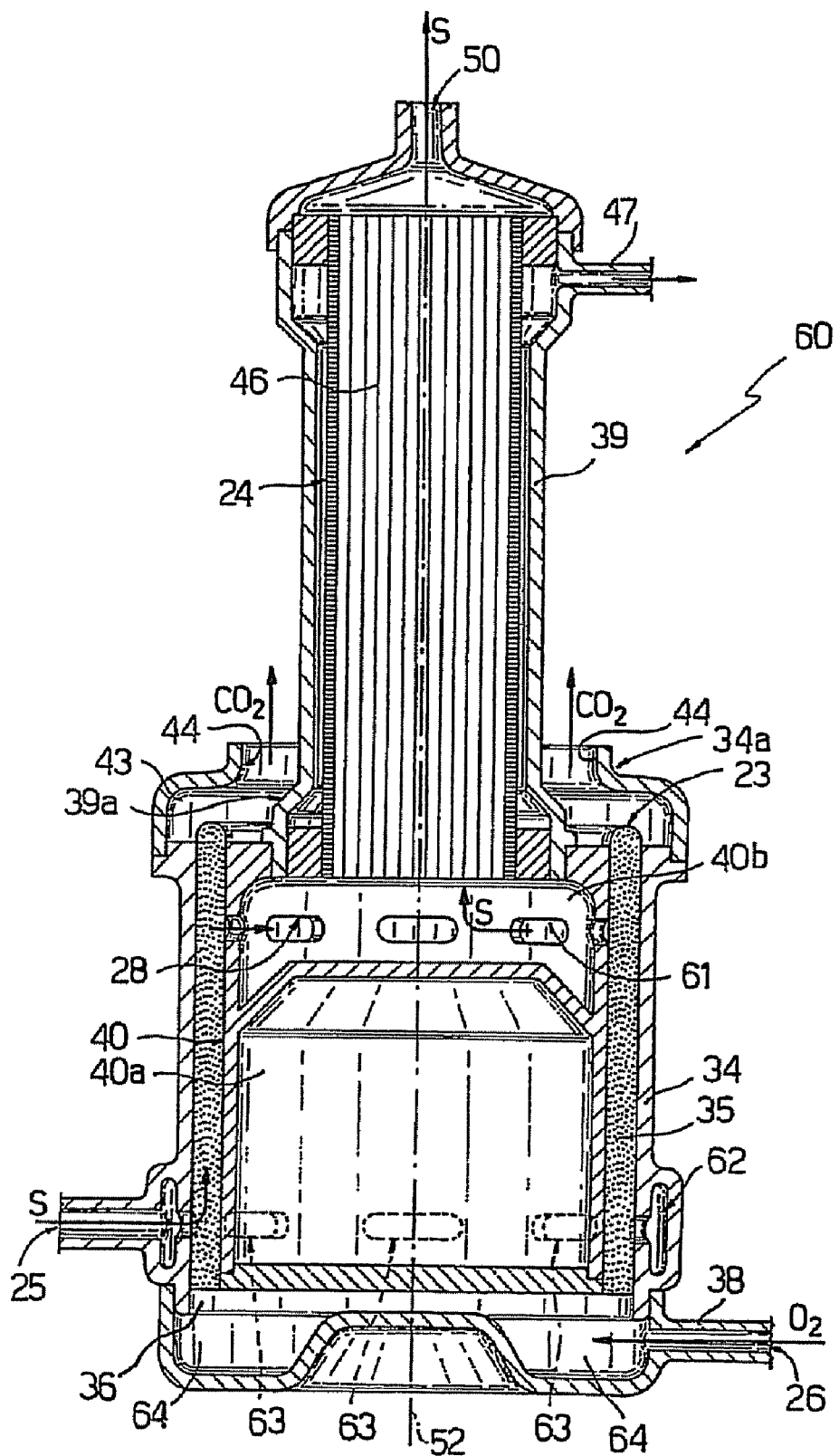
FIG. 3 is a cross-sectional view of an alternative treatment unit of FIG. 2.

The FIG. 3 embodiment relates to a treatment unit 60 similar to treatment unit 15, and the component parts of which are indicated, where possible, using the same reference numbers as for the corresponding parts of treatment unit 15.

Treatment unit 60 differs from treatment unit 15 by $CO_2$ removing device 23 being connected to filter 24 so that filter 24 projects outwards of, as opposed to being housed completely inside, $CO_2$ removing device 23.

More specifically, as opposed to being housed completely inside outer casing 34 (containing $CO_2$ removing device 23), inner casing 39 containing filter 24 projects outwards and upwards from outer casing 34.

In the configuration shown in the FIG. 3 example, inner casing 39 is connected to the top of outer casing 34, and extends upwards coaxially with the longitudinal axis 52 of treatment unit 60. More specifically, the base portion 39a of inner casing 39 is fixed rigidly, preferably heat sealed, to the top portion 34a of outer casing 34.

As shown in FIG. 3, bell-shaped member 40 of treatment unit 60 has no through holes 42 at the bottom, and is divided into two separate portions: a bottom portion 40a closed hermetically, and the outer lateral surface of which rests on membranes 35; and a top portion 40b having a number of through holes 61, each defining outlet 28 and through which the blood deprived of $CO_2$ flows from $CO_2$ removing device 23 to filter 24. Top portion 40b is also connected to filter 24 by one or more conduits (not shown) by which the blood deprived of $CO_2$ flows into filter 24.

Inlet 25 of $CO_2$ removing device 23 is connected to an annular conduit 62 formed in the outer lateral wall of outer casing 34, which has a number of inner through holes 63 facing, and through which the pressurized blood flows towards, membranes 35.

In addition to the above, the bottom end of the bundle of membranes 35 is connected rigidly to the bottom end of outer casing 34 by supporting plate 36, which extends outwards to define, with the inner wall of the bottom end, a bottom gap 64 communicating with the outside of outer casing 34 via oxygen inlet channel 38 defining inlet 26 of $CO_2$ removing device 23.

In actual use, the blood to be filtered flows into $CO_2$ removing device 23 through inlet 25, into annular conduit 62, and out through holes 63 so as to flow under pressure to the bottom of the bundle of membranes 35. The pressurized blood forced upwards flows over and/or through membranes 35, while, at the same time, the pressurized oxygen flowing in from channel 38 and through bottom gap 64 is directed towards the bottom of the bundle of membranes 35, flows through membranes 35, and gradually upwards in the same direction as the blood flow. As the blood and oxygen flow through hollow fibres, the haemoglobin in the blood acquires oxygen and releases excess $CO_2$, which flows to the top of outer casing 34, through a top gap 43, and out through exhaust channel 44.

$CO_2$ removal is completed by the time the blood reaches the top of the bundle of membranes 35, where through holes 61 feed the flow of the blood deprived of $CO_2$ along respective conduits (not shown) to the inlet (not shown) of inner casing 39, inside which filtration takes place.

The blood then flows through semi-permeable membranes 46, which separate the blood from the waste substances and/or toxic substances and surplus liquids, which are expelled from inner casing 39 along drain channel 47; and the pressurized blood is forced gradually towards outlet channel 50, from which it flows out purified.

Treatment units 15 and 60 described above may also be used to advantage in a machine for respiration support therapy only, e.g., in patients with no kidney malfunction; in which case, the ultrafiltrate from drain channel 47 of CO2 removing device 23 is obviously defined substantially by a dilution liquid, such as plasma water, and therefore contains no waste and/or toxic substances.

Figure 4:
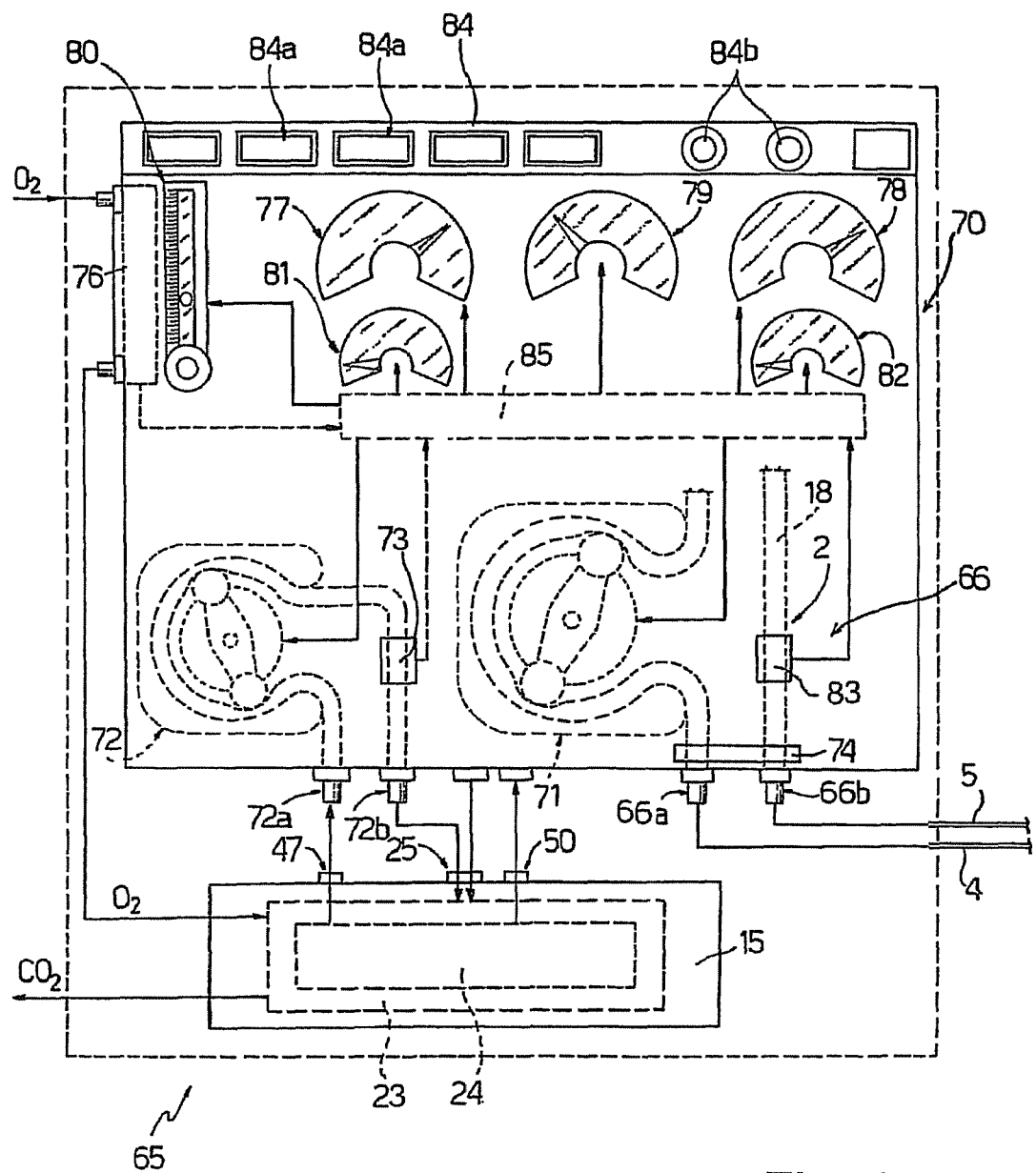
FIG. 4 is a schematic representation of a blood treatment apparatus in accordance with an embodiment of the present invention.

FIG. 4 shows one possible application of a treatment unit 15 (or 60) in a machine 65 for removing $CO_2$ from the blood, which therefore provides solely for respiration support therapy of a patient with no kidney malfunction.

Machine 65 substantially comprises a blood flow circuit 66 (shown partly in FIG. 4) connectable to the patient's cardiocirculatory system by catheters 4 and 5 for receiving blood from the patient and feeding it back, purified, to the patient; a treatment unit 15 (or 60) connected to blood flow circuit 66 to perform respiration support therapy; and an electronic control device 70 for coordinating the process for removing $CO_2$ from the blood and performed by treatment unit 15, and displaying a series of measuring parameters to monitor $CO_2$ removal continuously.

More specifically, electronic control device 70 comprises at least two blood flow pumps connected along blood flow circuit 66 (shown partly): a first flow pump 71, hereinafter indicated, which circulates the blood at a given flow rate along flow circuit 66 and through treatment unit 15; and a second flow pump, hereinafter indicated 72, which receives the ultrafiltrate from drain channel 47, and supplies it to treatment unit 15 to appropriately dilute the blood in $CO_2$ removing device 23.

As stated, the ultrafiltrate from drain channel 47 of filter 24, coming from a patient with healthy kidneys, substantially comprises a dilution liquid defined by plasma water (with no waste and/or toxic substances), so that treatment unit 15 operates in exactly the same way as a $CO_2$ removing device. That is, during blood purification, filter 24 simply removes the plasma water from the blood and feeds it to the $CO_2$ removing device, thus advantageously, ensuring the blood in $CO_2$ removing device 23 is diluted sufficiently.

In connection with the above, it should be pointed out that filter 24, by simply providing in this case for removing the plasma water from the blood, may conveniently be reduced, thus further reducing the overall size of treatment unit 15. More specifically, filter 24 is designed to remove enough plasma water from the blood to dilute the blood supplied to $CO_2$ removing device 23, thus eliminating the need to excessively "coagulate" the patient, while at the same time ensuring correct operation of membranes 35 even for prolonged periods (e.g., 24 hours).

It should also be pointed out that, in this case, besides drastically reducing blood flow resistance, thus reducing haemolysis, i.e. traumatic destruction of red blood cells, filter 24 also enables a sufficient pressure drop to be maintained in treatment unit 15 to prevent gas bubbles accidentally entering the blood, thus safeguarding the patient against gaseous embolisms.

With reference to FIG. 4, pump 72 has an inlet 72a connected to drain channel 47 of filter 24, and an outlet 72b connected to inlet 25 of treatment unit 15; and pump 71 is located along flow circuit 66, which has an inlet 66a connected to catheter 4 to receive the blood for $CO_2$ removal, and an outlet 66b connected by a conduit to catheter 5, which is inserted inside a vein to feed the blood deprived of $CO_2$ back into the patient's cardiocirculatory system.

In the FIG. 4 example, pumps 71 and 72 are defined by two peristaltic pumps, e.g., roller, one of which provides for circulating blood at a higher flow rate than the other. In the example shown, pump 71 may be designed for a flow rate of preferably about 350 ml/minute, and pump 72 is designed for a flow rate of preferably about 53 ml/minute.

Electronic control device 70 also comprises a first pressure detecting device 73 for supplying an output signal relative to the pressure of the ultrafiltrate supplied to $CO_2$ removing device 23 to dilute the blood, a second pressure detecting device 74 for supplying an output signal relative to the intake pressure of the blood from the patient, and an output signal relative to the feedback pressure of the blood to the patient's body.

Electronic control device 70 also comprises a detecting device 76, e.g., a flow gauge, for supplying an output signal relative to the oxygen flow rate to treatment unit 15.

With reference to FIG. 4, electronic control device 70 also comprises an ultrafiltrate pressure display device 77, a display device 78 showing the feedback pressure of the blood to the patient's body, an intake blood pressure display device 79, a display device 80 showing the oxygen flow rate to treatment unit 15, a display device 81 showing the flow of pump 71, i.e., the blood flow absorbed by the patient, and a display device 82 showing the flow of pump 72, i.e., ultrafiltrate flow to treatment unit 15.

Preferably, though not necessarily, electronic control device 70 also comprises a display device (not shown) showing the fall in pressure in the blood flow from pump 71 to treatment unit 15.

Electronic control device 70 also comprises a sensor 83 preferably located along connecting conduit 18 of blood flow circuit 66 for supplying an output signal relative to the presence of air or gas bubbles in the filtered feedback blood before it is fed back to the patient's body. Electronic control device 70 also comprises an acoustic/visual indicator device 84 for generating on command an acoustic/visual alarm signal to inform the operator of a possible malfunction of the machine and/or a patient hazard condition.

More specifically, in the FIG. 4 example, acoustic/visual indicator device 84 comprises a number of displays 84a and/or acoustic indicators 84b, each indicating a corresponding hazard condition or malfunction, such as a sudden fall in blood pressure between pump 71 and treatment unit 15, intake or feedback blood pressure or flow outside a predetermined safety range, low oxygen supply to treatment unit 15, or the presence of air bubbles in the blood.

Electronic control device 70 also comprises a central control block 85 for receiving the measured ultrafiltrate pressure signal from first pressure detecting device 73 and displaying it on display device 77, receiving the measured intake and feedback pressure signals from second pressure detecting device 74 and displaying them on display devices 78 and 79 respectively, and receiving the oxygen flow rate signal from detecting device 76 and displaying it on display device 80.

Central control block 85 also calculates, instant by instant, the blood flow supplied by pump 71 and the ultrafiltrate flow supplied by pump 72, and displays them on display devices 81 and 82, respectively.

Central control block 85 also receives the signal from sensor 83 and disables pumps 71 and 72 immediately if air bubbles are detected in the blood. When this occurs, central control block 85 preferably activates acoustic/visual indicator device 84 to inform the operator of a system malfunction and/or patient hazard condition.

Central control block 85 also determines, instant by instant, whether the intake or feedback blood pressure and/or flow values, the ultrafiltrate flow and/or pressure value, and the pressure drop conform with predetermined conditions on the basis of respective safety thresholds or ranges.

If one or more conditions are not conformed with, and/or if air bubbles are detected, central control block 85 disables pumps 71 and 72, cuts off blood feedback to the patient and oxygen supply to the treatment unit, and activates acoustic/visual indicator device 84 to inform the operator of a system malfunction and/or patient hazard condition. It should be pointed out that blood feedback to the patient and/or oxygen supply to the treatment unit may be cut off by central control block 85 commanding closure of a number of solenoid valves (not shown) installed along flow circuit 66 and at the oxygen inlet.

Figure 5:
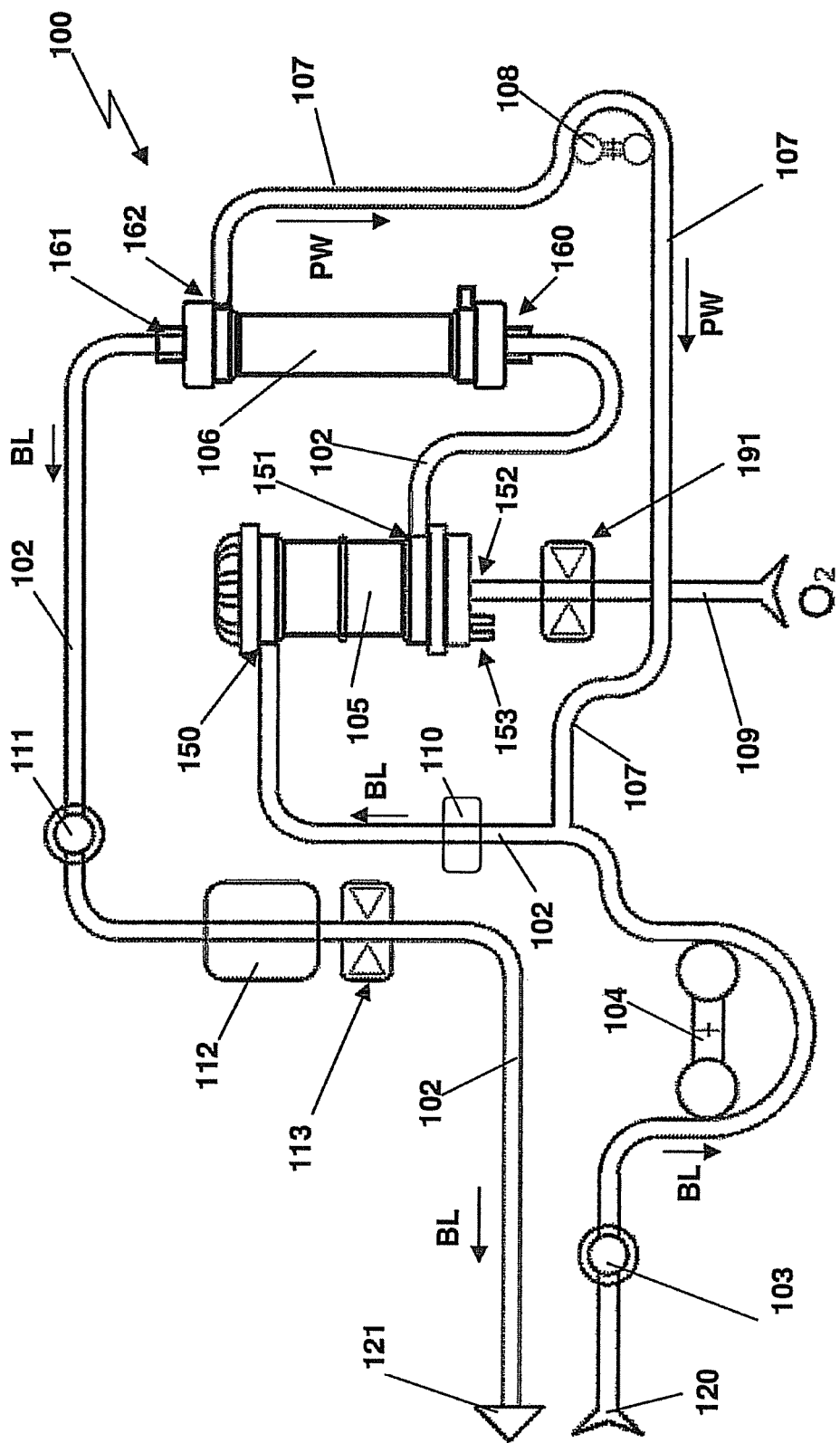
FIG. 5 is a schematic representation of a blood treatment apparatus in accordance with an embodiment of the present invention.

In a different embodiment shown in FIG. 5 the treatment apparatus 100 according to the present invention is provided with a $CO_2$ removing device and filter which are separate, i.e. not integrated in one body.

The apparatus 100 according to the invention can be connected to a patient by means of two catheters with a venovenous transcutaneous access. Circuit 102 illustrates the flow of blood into the apparatus 100. The circuit 102 can be connected to the patient so that said circuit receives the blood to be depurated and reintroduces the depurated blood into the patient. In particular, the circuit 102 can be connected by means of two input and output catheters which are respectively connected to the input 120 and to the output 121 of the circuit itself. Arrows BL indicate the direction of the path followed by the blood.

One of the advantages of this invention is that the apparatus can be used without exposing the vessels when in well-known respiratory support systems said exposition is necessary. As the flow is inferior to 400 ml/min, it is sufficient to use a 14 French bilumen catheter (4.66 mm diameter) and it is possible and preferable to carry out a veno-venous transcutaneous access into a peripheral vessel thanks to one of the methods which are available (e.g., the Seldinger method). This is not possible for systems based on much higher flows (ECMO) for which the surgical exposition of the vessel (central) and a subsequent cannuling are necessary.

A suction sensor 103, whose function is that of detecting the input pressure in the circuit 102, is located downstream of the input 120.

A pump 104 is located downstream of the sensor 103 and said pump pushes the blood downstream where a hoxygenator 105 is positioned. The hoxygenator 105 is also called a "decapneizator" and is a device provided with membrane for removing the $CO_2$ from the blood.

The hoxygenator 105 is provided with a first input 150 for the blood to be treated, with a first output 151 for the treated blood, with a second input 152 for the oxygen and with a second output 153 for the carbon dioxide that has been separated from the blood. The second input 152 is connected to an oxygen source by means of a corresponding duct 109 on which an intercepting device 191, which is also called "clamp", is advantageously foreseen. Said intercepting device 191 closes the 109 duct when the circuit is disabled, that is to say when the pump 104 is disabled. A plurality of ducts and of membranes which allow the oxygen to interact with the blood so as to determine the release of $CO_2$ and its exit from the device 105 are foreseen inside the hoxygenator. The hoxygenator 105 is known so it will not be described in detail.

The output 151 of the hoxygenator 105 is connected downstream to an input 160 of a haemofilter 106. The haemofilter 106 separates part of the plasmatic water from the blood received from the hoxygenator 105.

The haemofilter 106 is provided with two outputs: the first output 161 is connected to the circuit 102 and is used to convey the treated blood downstream. And the second output 162 from which the plasmatic water exits. A duct 107 is connected to the output 162 and said duct 107 is connected to the depuration circuit 102 at a point disposed upstream of the hoxygenator 105. On the duct 107 is disposed a pump 108 which pushes the plasmatic water upstream, to the point disposed upstream of the hoxygenator 105. In FIG. 5 indicates with PW the direction of the plasmatic water flow. Upstream of the hoxygenator 105a sensor 110 can be disposed for detecting the pressure.

Downstream of the haemofilter 106, on the duct 102, a pressure sensor 111 can be disposed for detecting the so called "venous resistance", an air bubble sensor 112 for detecting the possible presence of air bubbles and an intercepting device 113 or "clamp" for closing the duct if necessary.

The depuration circuit 102 ends in correspondence of the output catheter which is connected to the end 121 of the duct so as to reintroduce the depurated blood into the patient.

Functioning occurs when the apparatus 100 has been connected to the patient by means of the input and output catheters (with a venovenous transcutaneous access), and the pump 104, which pushes the blood downstream, is enabled.

The blood reaches the hoxygenator 105 and, from there, it reaches the haemofilter 106. At this point, a blood component relevant to the plasmatic water is used to dilute the blood as it is taken upstream of the hoxygenator by means of the duct 107 pushed by the pump 108. This feature provides many advantages including reducing the hematocrit due to a dilution of around 20% and this reduction reduces the resistance to the blood flow inside the decapneizator. As a consequence of this reduction and the hemolysis, as well as the heparin dosing, the removal of $CO_2$ from the plasmatic water which conveys part of it is allowed. Moreover, the presence of the haemofilter represents an important safety factor as it increases the resistance to blood flow inside the circuit so as to increase its pressure and to prevent the gas under pressure inside the decapneizator from entering the blood flow as this might cause the formation of emboli.

All the sensors described above, as well as the pumps motorization means and the enabling means for the intercepting devices, are connected to electric control means which can be set according to the requested therapy. Said command and control organs of the elements described above and illustrated in the enclosed drawings are usually well-known to the technicians who work in this field, and therefor are not described in detail.

The invention provides a blood treatment method which can be used for the simultaneous extrarenal blood purification therapy and respiration support therapy or only for the respiration support therapy.

According to the method of the present invention, a blood purification circuit is connected to a patient's cardiocirculatory system by two blood feed conduits or catheters, one of which receives and supplies blood from the patient's vein to blood purification circuit, while the other is inserted inside a vein to feed the purified blood back into the patient's cardio-circulatory system. The blood in the purification circuit passes through a $CO_2$ removing means, having at least a first inlet for receiving a flow of blood for $CO_2$ removal and at least a first outlet for the flow of blood deprived of $CO_2$, and through filtering means having at least a first inlet for receiving a flow of blood for purification, and at least a first outlet for the flow of purified blood.

The diluting liquid obtained from the blood, liquid which is expelled during purification of the blood in said filtering means, is supplied to the $CO_2$ removing means by a drain channel (47, 107) which is connected directly to said first inlet (25, 150) of said $CO_2$ removing means (23, 105). Moreover, in correspondence with said drain channel (47, 107) a pump provides supply of said diluting liquid to the $CO_2$ removing means at a flow rate of about 53 ml/min and said blood purification circuit comprises a pump (3, 104) located along said blood purification circuit pumping the blood at a flow rate of about 350 ml/min.

While the invention has been described with respect to a specific embodiment thereof, it will be understood by those skilled in the art that variations and modifications may be made without departing from the essential features thereof.

What is claimed is:

1. A blood treatment method for the simultaneous extrarenal blood purification therapy and respiration support therapy, comprising:
    providing a blood purification circuit connected to a patient's cardiocirculatory system by two blood feed conduits, the circuit comprising:
        a first conduit for receiving blood from the patient's cardiocirculatory system and supplying blood to the blood purification circuit,
        a second conduit in communication with a patient's vein to feed purified blood back into the patient's cardiocirculatory system,
        a filtering means, comprising a first inlet for receiving blood for purification in communication with the blood purification circuit, and a first outlet for expelling purified blood,
        a $CO_2$ removing means, comprising a first inlet for receiving a flow of blood for $CO_2$ removal and a first outlet for expelling blood deprived of $CO_2$, and
        a drain channel for directing a diluting liquid separated from the purified blood by the filtering means to the $CO_2$ removing means, wherein the drain channel is directly connected to the first inlet of the $CO_2$ removing means,
    directing blood through the filtering means;
    directing blood through the $CO_2$ removing means; and
    supplying the diluting liquid to the $CO_2$ removing means through the drain channel which is directly connected to the first inlet of the $CO_2$ removing means.

2. The blood treatment method of claim 1, wherein the first outlet of the $CO_2$ removing means is connected to the first inlet of the filtering means to supply to the filtering means blood deprived of $CO_2$.

3. The blood treatment method of claim 1, further comprising a pump for supplying the diluting liquid to the $CO_2$ removing means at a flow rate of about 53 ml/min.

4. The blood treatment method of claim 1, further comprising a pump for pumping the blood within the blood purification circuit at a flow rate of about 350 ml/min.

5. The blood treatment method of claim 1, further comprising a pump for supplying the diluting liquid to the $CO_2$ removing means at a flow rate of about 53 ml/min, and a pump for pumping the blood within the blood purification circuit at a flow rate of about 350 ml/min.

6. A blood treatment unit for simultaneous extrarenal blood purification therapy and respiration support therapy, comprising:
    $CO_2$ removing means comprising a first inlet for receiving a flow of blood for $CO_2$ removal, and a first outlet for expelling blood deprived of $CO_2$; and
    filtering means comprising a first inlet for receiving the flow of blood, a first outlet for expelling purified blood, and at least one drain channel by which, in use, a diluting liquid obtained from the blood is expelled during purification of the blood;
    wherein the drain channel is directly connected to the first inlet of the $CO_2$ removing means to supply the diluting liquid to the $CO_2$ removing means, without submitting the diluting liquid to any filtering treatment during passage along the drain channel.

7. The blood treatment unit of claim 6, further comprising pumping means connecting the drain channel of the filtering means to the first inlet of the $CO_2$ removing means to pump the diluting liquid, obtained from the blood by the filtering means, to the $CO_2$ removing means.

8. The blood treatment unit of claim 6, wherein the filtering means are at least partially integrated with the $CO_2$ removing means.

9. The blood treatment unit of claim 8, wherein the $CO_2$ removing means further comprises an inner seat which houses the filtering means.

10. The blood treatment unit of claim 6, wherein the $CO_2$ removing means further comprises a first casing having at least one membrane for removing $CO_2$ from the blood.

11. The blood treatment unit of claim 10, wherein the $CO_2$ removing means further comprises a first casing having a plurality of membranes for removing $CO_2$ from the blood.

12. A blood treatment unit for simultaneous extrarenal blood purification therapy and respiration support therapy, comprising:
    a $CO_2$ removing means, comprising a first inlet for receiving a flow of blood for $CO_2$ removal, and a first outlet for expelling blood deprived of $CO_2$;
    a filtering means, comprising a first inlet for receiving a flow of blood for purification, and a first outlet for expelling purified blood, wherein the first outlet of the $CO_2$ removing means is connected to the first inlet of the filtering means to supply to the filtering means blood deprived of $CO_2$, the filtering means further comprising at least one drain channel by which, in use, a diluting liquid obtained from the blood is expelled during purification of the blood, the drain channel being directed connected to the first inlet of the $CO_2$ removing means to supply the diluting liquid to the $CO_2$ removing means;
    wherein the $CO_2$ removing means comprises an inner seat housing the filtering means, and a first casing having at least one membrane for removing $CO_2$ from the blood; and
    wherein the filtering means comprises a second casing housed inside the first casing having at least one blood purifying membranes.

13. The blood treatment unit of claim 12, wherein the first casing comprises a plurality of membranes for removing $CO_2$ from the blood.

14. The blood treatment unit of claim 13, wherein the membranes for removing $CO_2$ from the blood are interposed between the first casing and the second casing.

15. The blood treatment unit of claim 13, wherein the $CO_2$ removing means comprise a container internally defining the inner seat, interposed between the membranes for removing $CO_2$ from the blood and the second casing.

16. The blood treatment unit of claim 12, wherein the second casing comprises a plurality of blood purifying membranes.

* * * * *